US006200579B1

(12) United States Patent
Picard

(10) Patent No.: US 6,200,579 B1
(45) Date of Patent: *Mar. 13, 2001

(54) USE OF A TWO-PHASE COMPOSITION FOR MAKE-UP REMOVAL OF TRANSFER-FREE MAKE-UP COMPOSITIONS

(75) Inventor: Elisabeth Picard, Velizy (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/921,333

(22) Filed: Aug. 29, 1997

(30) Foreign Application Priority Data

Sep. 6, 1996 (FR) .................................................. 96 10923

(51) Int. Cl.⁷ ...................................................... A61K 6/00
(52) U.S. Cl. ........................ 424/401; 424/70.7; 424/70.6; 424/70.1; 424/64
(58) Field of Search ........................... 424/401, 64, 70.7, 424/70.6, 70.1; 514/846; 510/136

(56) References Cited

U.S. PATENT DOCUMENTS

| 5,468,496 | * | 11/1995 | Touzan et al. | 424/401 |
| 5,474,777 | * | 12/1995 | Marion et al. | 424/401 |
| 5,505,937 | * | 4/1996 | Castrogiovanni et al. | 424/64 |
| 5,871,758 | * | 2/1999 | Nagy et al. | 424/401 |

FOREIGN PATENT DOCUMENTS

| 0 370 856 | 5/1990 | (EP) . |
| 0 490 750 | 6/1992 | (EP) . |
| 0 490 749 | 6/1992 | (EP) . |
| 0 603 080 | 6/1994 | (EP) . |

* cited by examiner

Primary Examiner—Robert H. Harrison
(74) Attorney, Agent, or Firm—Oblon, Spivak, McClelland, Maier & Neustadt, P.C.

(57) ABSTRACT

An applied make-up of long durability and/or a transfer-free make-up composition is removed from the skin by applying to the skin a composition consisting of an aqueous phase and an oily phase, which are distinct, to remove the make-up or transfer-free make-up.

3 Claims, No Drawings

USE OF A TWO-PHASE COMPOSITION FOR MAKE-UP REMOVAL OF TRANSFER-FREE MAKE-UP COMPOSITIONS

BACKGROUND OF THE INVENTION

1. Field of the Invention

The present invention relates to a composition consisting of an aqueous phase and a distinct oily phase for make-up removal of make-ups of long durability and/or of transfer-free make-up compositions. More particularly, the invention relates to a make-up remover consisting of two distinct phases of an aqueous phase and an oily phase, for the removal of make-ups applied to the skin from transfer-free and/or long durability make-up compositions.

2. Description of the Background

Lip rouge and foundation compositions generally include fatty substances such as waxes and oils as well as a particulate phase generally made up of fillers and pigments. When applied to the skin or the lips, these compositions have the disadvantage of transferring, that is to say of being at least partially deposited, leaving a mark, on some substrates with which they may be brought into contact, especially a glass, a cup, a garment or the skin. The result is a mediocre persistence of the film on the skin or on the lips, making it necessary to renew at regular intervals the application of the foundation or lip rouge composition. Moreover, the appearance of unacceptable marks on some garments and especially on blouse collars can persuade some women to not use make-up of this type.

A new generation of so-called "nontransfer" and/or "long-durability" make-up products has appeared recently. These new products differ from those already known in view of their use of volatile oils instead of the heavier oils usually employed. In particular, the lip rouge compositions and the nontransfer foundations include silicone oils which have not been employed in the lip rouge compositions of the prior art.

Japanese Application No. 61-65809 shows "transfer-free" lip rouge compositions containing from 1–70% by weight of liquid silicone resin with silicate repeat units (or with a three-dimensional network) comprising pendent alkyl chains of 1–6 carbon atoms or phenyl, 10–98% by weight of a volatile silicone oil with a cyclic Si—O chain and with methyl radicals, and pulverulent fillers.

U.S. Pat. No. 5,505,937 describes "transfer-free" compositions containing 1–70% of a volatile silicone oil, 0.1–15% of a silicone resin, 10–45% of a wax, 5–50% of particulate compounds and 1–30% of oil.

French Application No. 95-09254 relates to "transfer-free" make-up compositions which comprise a combination of a phenylated silicone oil and of a volatile compound in a fatty phase and preferably including less than 20% by weight of nonvolatile hydrocarbon oil.

French Application No. 96-07107 relates to "transfer-free" make-up compositions which comprise a volatile silicone oil and a silicone wax which is solid or semisolid at ambient temperature.

French Application No. 96-08420 relates to "transfer-free" make-up compositions which comprise the combination of a volatile compound and of a pasty fatty compound in order to decrease the transfer and/or the migration, and/or to improve the durability of the composition. Since volatile oils have a tendency to evaporate rapidly, the newer lip rouge and foundation compositions exhibit the particular property of forming a film of solid fatty substance when they are applied to the lip mucosa and to the skin.

In contrast to the lip rouge compositions of the prior art, which do not require make-up removal, the long-durability and/or transfer-free lip rouge compositions must be removed at the end of the day by a specific make-up removal from the lips. However, it has been found that long-durability and/or transfer-free lip rouge and foundation compositions are more difficult to remove than conventional make-up compositions. A need, therefore, continues to exist for a composition which allows satisfactory make-up removal of the transfer-free make-up compositions.

The discovery of the present invention is that the use of two-phase compositions makes it possible to remove a very durable and/or transfer-free make-up perfectly and with great ease, under highly satisfactory conditions of comfort, in particular of coolness.

Make-up removal compositions consisting of two distinct phases, also called "two-phase compositions" are known in the field for make-up removal from the area of the eyes. However, make-up products for the eyes are very different from the compositions for making-up the lips and from foundations.

In addition, make-up products for the eyes are applied by a gentle touch by merely dabbing the like of the eyelids with a paintbrush or brush, whereas lip rouge compositions are applied by exerting a considerable pressure on the lips, and foundations are applied by massaging the skin, with some manual pressure. Moreover, the lip mucosa has a special morphology in which the epidermis is thin and fragile and the dermis is richly vascularized and enervated. These morphological characteristics endow it with an affinity for make-up products which differs greatly from those of the eyelids or of the keratinous fibers forming the eyelash.

Consequently, there is nothing to suggest that two-phase compositions employed for make-up removal especially of mascaras would be capable of being employed successfully in make-up removal of transfer-free compositions.

SUMMARY OF THE INVENTION

Accordingly, one object of the present invention is to provide a method of removing make-ups of long durability and/or transfer free compositions.

Briefly, this object and other objects of the present invention as hereinafter will become more readily apparent can be attained by a method of removing an applied make-up of long durability and/or a transfer-free make-up composition from the skin by applying to the skin a composition consisting of an aqueous phase and an oily phase, which are distinct, to remove the make-up or transfer-free make-up.

DETAILED DESCRIPTION OF THE PREFERRED EMBODIMENTS

The invention is directed preferably to make-up compositions which can be in the form of a make-up product for the skin, in particular a foundation, a blusher or eye shadow or a lip rouge.

It applies in particular to the make-up compositions described in JP-A-61-65809, U.S. Pat. No. 5,505,937, FR-95-09254, FR-96-07107 and FR-96-08420, the contents of U.S. Pat. No. 5,505,937 being incorporated in the present text by reference.

The invention applies more particularly to the make-up removal of transfer-free lip rouge and foundation compositions. It applies more especially to the make-up compositions which comprise a volatile oil, fatty substances and a particulate phase.

In particular it applies to the compositions comprising:
   1–90%, preferably from 10–70% by weight, of a volatile oil, more preferably still from 20–60% by weight of a volatile oil,
   an optional silicone-containing compound selected from the group of silicone waxes, silicone resins, silicone oils, optionally phenylated, and a pasty fatty substance, up to 50% by weight of a fatty phase consisting of conventional fatty substances (waxes and/or oils), from 0–30%, preferably from 5–25% by weight of a particulate phase.

The transfer-free make-up compositions applicable to the invention, therefore, include at least one volatile oil which may be selected in particular from hydrocarbon oils and silicone oils, cyclic or linear ones, alone or as a mixture.

A volatile oil as described above is any oil which is capable of evaporating upon contact with the skin. Oils which are preferably employed are those whose flash point is sufficiently high to allow these oils to be employed in formulation, and sufficiently low to obtain the desired evanescent effect. Oils whose flash point is of the order of 40–100° C. are preferably employed. Suitable volatile silicone oils include cyclotetradimethylsiloxane, cyclopentadimethylsiloxane, cyclohexadimethylsiloxane and methylhexyldimethylsiloxane. Suitable isoparaffins include the volatile hydrocarbon oils.

The particulate phase may include pigments and/or mothers-of-pearl and/or fillers usually employed in cosmetic compositions.

Pigments are to be understood to mean inorganic or organic white or colored particles intended to color and/or opacify the composition. Fillers should be understood to mean mineral or synthetic, lamellar or nonlamellar colorless or white particles intended to impart "body" or rigidity to the composition and/or softness, mattness and uniformity to the make-up. Mothers-of-pearl are intended to mean iridescent particles which reflect light.

The pigments may be present in the composition in an amount of 0–15% by weight of the final composition and preferably in an amount of 8–10% by weight. They may be white or colored, inorganic and/or organic, of usual or nanometric size. Pigments include dioxides of titanium, zirconium and cerium, as well as oxides of zinc, iron and chromium, ferric blue, carbon black, ultramarines (aluminosilicate polysulphides), manganese pyrophosphate and some metal powders such as those of silver and aluminum. Lakes commonly employed to give the lips and the skin a make-up effect, which are calcium, barium, aluminum and zirconium salts of acidic dyes such as haloacidic, azo, anthraquinone and similar dyes, are also included. The mothers-of-pearl may be present in the composition in an amount of 0–20%, preferably in an amount of the order of 8–15% of the total weight of the composition. Among the mothers-of-pearl which can be envisaged are included natural mother-of-pearl, mica covered with titanium oxide, iron oxide, natural pigment and bismuth oxychloride, as well as colored titanium mica.

The fillers, which may be present in an amount of 0–30% by weight, preferably 5–15% of the total weight of the composition, may be inorganic or synthetic, lamellar or nonlamellar. Talc, mica, silica, kaolin, nylon and polyethylene powders, Teflon, starch, boron nitride, microspheres such as Expancel (Nobel Industrie), polytrap (Dow Corning) and silicone resin microbeads (for example Tospearls from Toshiba) are included.

The composition of the invention may also include at least one optionally silicone-containing compound selected from the group of silicone waxes, silicone resins, optionally phenylated silicone oils and a pasty fatty substance.

The said pasty fatty substance is preferably hydrocarbon-containing, may be a polymer, and may also be silicone- and/or fluorine-treated; it may also be in the form of a mixture of various hydrocarbon and/or silicone and/or fluorine compounds. In the case of a mixture, the hydrocarbon-containing pasty compounds are preferably employed in major amounts.

The pasty fatty compounds of the invention can be defined in terms of at least one of the following physico-chemical properties:

(i) a viscosity of 0.1–40 Pa•s (1–400 poises), preferably 0.5–25 Pa•s, measured at 40° C. with a Contraves TV rotary viscometer equipped with an MS-r3 or MS-r4 rotor, at the frequency of 60 Hz, and (ii) a melting point of 25–70° C., preferably 25–55° C.

One skilled in the art can choose the rotor enabling the viscosity to be measured from the MS-r3 and MS-r4 rotors, on the basis of general knowledge, so as to be able to carry out the measurement of the pasty compound which is tested.

Among the pasty compounds capable of being employed within the scope of the present invention are lanolins or lanolin derivatives which have a viscosity of 18–21 Pa•s, preferably 19–20.5 Pa•s, and/or a melting point of 30–60° C. Fatty esters may also be mentioned, especially those which have 20–45 carbon atoms (melting point of the order of 25–70° C.) and triglycerides such as hydrogenated vegetable oils. Arachidyl propionate, polyvinyl laurate and cholesterol esters may be included among the esters.

Silicone-containing pasty fatty substances may also be mentioned such as alkyldimethicones, which have a melting point of 25–60° C., especially those sold by Dow Corning under the trade names of DC2503 and DC25514.

Any conventional oil thickened with the aid of a conventional thickening agent can also be employed.

The oils capable of being thickened include oils of animal, vegetable, mineral and/or synthetic origin, such as silicone, and optionally phenylated, oil.

The thickening agent can be selected from clays such as bentonites or hectorites, optionally modified especially with distearyldimethylammonium chloride or with stearyldimethylbenzylammonium chloride, or with aluminum or magnesium silicates or else with conventional polymers which are known to be capable of thickening oils. Hydrogenated castor oil derivatives such as "Thixinr" from Rheo. can also be employed.

The pasty compound(s) may be present in an amount of 1–40% by weight, preferably in an amount of 8–35% by weight and, more preferably still, in an amount of 15–30% by weight, relative to the total weight of the composition.

The phenylated silicone oils include a polyphenylmethylsiloxane or a phenyltrimethicone or a mixture of various phenylated silicone oils, and in particular have the following formula:

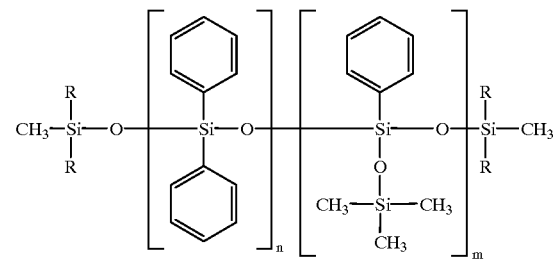

in which

R is a $C_1$–$C_{30}$ alkyl radical, an aryl radical or an aralkyl radical, n is an integer of 0–100, m is an integer of 0–100, provided that the sum m+n is of 1–100.

R is preferably a methyl, ethyl, propyl, isopropyl, decyl, dodecyl or octadecyl radical or else a phenyl, tolyl, benzyl or phenethyl radical.

Wacker Belsil PDM1000 oil, Dow Corning DC556 or SF558 oils, Goldschmidt Abil AV8853 oil or Rhône Poulenc Silbione 70633V30 oil are included among these phenylated oils.

The silicone waxes may be solid or semisolid at ambient temperature. These waxes may be in the form of a paste or of a rigid solid. In particular, these waxes have a melting temperature higher than 25° C. and, better, higher than 45° C.

The silicone waxes of the composition of the invention may have the following formula:

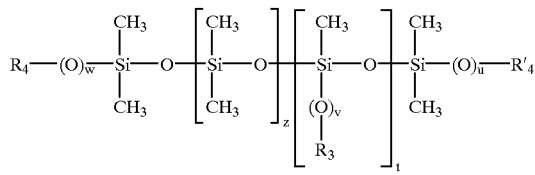

in which $R_3$, $R_4$ and $R'_4$ denote, independently of one another, a methyl group or hydrogen or a linear or branched alkyl chain containing from 10–45 carbon atoms, z and t denote, independently, an integer ranging from 0–100, u, v and w denote, independently, 0 or 1, on condition that t is other than 0 and $R_3$ other than methyl and hydrogen when $R_4$ and $R'_4$ denote methyl or hydrogen and that $R_4$ or $R'_4$ is other than methyl or hydrogen when $R_3$ denotes methyl or hydrogen or when t has the value 0.

In particular, $R_3$, $R_4$ or $R'_4$ denotes a linear chain containing 12–35 carbon atoms and, better, from 18–28 carbon atoms, like, for example, the radicals $C_{16}H_{33}$, $C_{18}H_{37}$, $C_{24}H_{49}$, $C_{26}H_{53}$ or a mixture of these radicals. $R_3$ is preferably an alkylated chain and $R_4$ the methyl group, u, v and w are equal to 0, z has a value from 2–40 and t has a value from 45–98.

Among the silicone waxes which can be employed in the invention are behenoxydimethicone (with $R_4=CH_3(CH_2)_{21}$, t=0, u=1, w=1, z<10) such as that sold by Goldschmidt under the name Abil Wax 2440, stearyldimethicone (with u=0, v=w=0, $R_4=CH_3$ and $R_3$=stearyl) such as that sold by Dow Corning under the name DC 2503, cetyldimethicone (with u=v=W=0, $R_4=CH_3$ and $R_3$=cetyl) such as that sold by Goldschmidt under the name Abil Wax 9814, stearylmethicone (with z=u=w=v=0, $R_4=CH_3$ and $R_3$=stearyl), such as that sold by Goldschmidt under the name Abil Wax 9809, $C_{24}$–$C_{28}$-alkyldimethicone (with u=v=w=0, $R_4=CH_3$ and $R_3$ is a $C_{24}$–$C_{28}$ alkyl and z<5) such as that sold by Goldschmidt under the name Abil Wax 9810, $C_{30}$–$C_{45}$-alkylmethicone (with z=u=v=w=0, $R_4=CH_3$ and $R_3$=a $C_{30}$–$C_{45}$ alkyl group) such as that sold by Goldschmidt under the name Abil Wax 9811 and stearoxydimethicone (with z=u=v=w=0, $R_4=CH_3$ and $R_3$=stearyl) such as that sold by Goldschmidt under the name Abil Wax 2434.

Alkyldimethicone polymers are included as other silicone waxes that can be employed in the invention.

These copolymers are especially those described in documents U.S. Pat. No. 5,338,536, U.S. Pat. No. 5,397,566, U.S. Pat. No. 5,541,276, U.S. Pat. No. 5,626,857, U.S. Pat. No. 5,061,481 and U.S. Pat. No. 5,397,566 and may have the following formula:

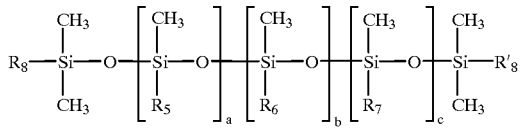

in which $R_5$, $R_6$, $R_7$, $R_8$ and $R'_8$ denote, independently of one another, methyl or hydrogen or a linear or branched alkyl or alkoxy chain which has from 5–36 carbon atoms, a and b denote, independently, an integer ranging from 1–50, and c denotes an integer ranging from 0–50, on condition that two of the radicals $R_5$, $R_6$, $R_7$, $R_8$ and $R'_8$ are other than the methyl group or hydrogen and are different from one another.

In particular, $R_5$ and $R_6$ denote a linear chain containing 10–20 carbon atoms, with $R_5$ other than $R_6$, $R_8$ and $R'_8$ are the methyl group, a ranges from 8–18, b ranges from 2–12, c has the value 0.

The remarkable effectiveness of the two-phase make-up-removal compositions is particularly obvious when they are applied to transfer-free make-up compositions including less than 20% of nonvolatile hydrocarbon oils, more particularly less than 5%, and more particularly still to make-up compositions that do not include any nonvolatile hydrocarbon oils, these compositions being known for their excellent resistance to transfer.

More particularly the subject-matter of the invention is the use of a composition consisting of an aqueous phase and of a distinct oily phase for make-up removal of transfer-free lip rouge compositions.

The make-up removal composition of the invention includes at least one aqueous phase and a distinct oily phase.

The aqueous phase of the make-up removal composition of the invention includes sterile demineralized water and/or a floral water such as rose water, cornflower water, camomile water or lime water or a natural thermal or mineral water like, for example: Vittel water, Vichy basin waters, Uriage water, La Roche Posay water, La Bourboule water, Enghien-les-Bains water, Saint Gervais-les-Bains water, Néris-les-Bains water, Allevar-les-Bains water, Digne water, Maizières water, Neyrac-les-Bains water, Lons-le-Saunier water, Les Eaux Bonnes, Rochefort water, Saint Christau water, Fumades water and Tercis-les-Bains water, Avene water.

The oily phase of the make-up removal composition of the invention includes or consists of a mixture of oils, it being possible for the latter to be mineral, vegetable or synthetic oils or else silicone oils.

Among the mineral oils which may constitute the oily phase are, in particular, liquid petrolatum and higher aliphatic hydrocarbons such as, for example isohexadecane; among the vegetable oils, jojoba oil and safflower oil; among the optionally volatile silicone oils, the cyclopentadimethylsiloxane sold under the name of "Volatil Silicone 7158" by Union Carbide and, among the synthetic products, alkyl palmitates, the alkyl group containing from 2–10 carbon atoms, such as isopropyl palmitate or 2-ethylhexyl palmitate, and alkyl adipates, the alkyl group containing from 2–10 carbon atoms, such as di-2-ethylhexyl adipate.

According to a particular embodiment of the invention the oily phase contains at least one alkyl palmitate, the alkyl group containing from 2–10 carbon atoms, in an amount of at least 8% and preferably of 10–30% relative to the total weight of the make-up removal composition.

According to a preferred form of the invention the oily phase contains at least one silicone oil in an amount of at least 8% and preferably of 15–50% relative to the total weight of the make-up removal composition.

The two-phase composition preferably additionally includes at least one surface-active agent in either of the phases.

The surface-active agent, which may be of the anionic, nonionic or amphoteric type, but preferably of the nonionic type, is preferably present in the aqueous phase in an amount of 0.1–10% (of active substance) by weight relative to the total weight of the make-up removal composition, and still more preferably of 0.5–3%.

Among the nonionic surface-active agents those particularly preferred are:

polyoxyethylenated sorbitol fatty esters such as the product sold under the name of "Tween 20" by Atlas, polyoxyethylenated fatty alcohols such as the product sold under the name of "Remcopal 21912 AL" by Gerland, polyoxyethylenated alkylphenols such as the product sold under the name of "Triton X 100" by Rohm-Haas, and condensates of ethylene oxide and of propylene oxide such as those sold under the names of "Synperonic PE" by ICI and in particular identified as L 31, L 64, F 38, F 88, L 92, P 103, F 108 and F 127.

The anionic surface-active agents include especially:

alkyl ether sulfates such as the product sold under the name of "Texapon ASV" by Henkel, alkyl sulfoacetates such as the products sold under the name of "Lathanol LAL" by Stepan, alkyl sulfosuccinates such as the product sold under the name "Sodium dioctyl sulphosuccinate" by Rhone Poulenc, alkylamido sulfosuccinates such as the product sold under the name "Rewoderm S 1333" by Rewo, alkylamido polypeptides such as the product sold under the name "Lamepon S" by Grunau, and acylsarcosinates such as the product sold under the name "Oramix L 30" by Seppic.

The amphoteric surfactants include especially:

alkylamidopropyl dimethylbetaines such as the product sold under the name "Tego Betaine L 7" by Goldschmidt, alkylamidobetaines such as the product sold under the name "Incronam 30" by Croda, imidazoline derivatives such as the product sold under the name "Chimexane HD" by Chimex, and N-alkyl-b-iminodipropionates such as the product sold under the name "Monateric ISA 35" by Mona.

The weight ratio of the aqueous phase and the oily phase is preferably from 30/70–60/40.

The make-up removal composition of the invention may also contain conventional cosmetic adjuvants which will be found in either phase, depending on their hydrophilic or lipophilic nature, such as, for example, perfumes, preserving agents, dyes, softeners, a buffer, moisturizers and optionally an electrolyte such as sodium chloride to impart isotonicity to the aqueous phase.

Moistening agents which may be mentioned in particular include hexylene glycol and polyethylene glycol 600, these being present in a concentration ≦5% and preferably of 0.05–2% of the total weight of the composition.

Allantoin and some plant extracts are included in particular among the softening agents.

Such make-up removal compositions have been described especially in U.S. Pat. No. 5,165,917, the content of which is incorporated hereinafter by reference. According to the invention the make-up removal composition may also preferably include in the aqueous phase, a dephasing agent in an amount especially of 0.025–5% of the total weight of the composition, the agent being an alkyldimethylbenzylammonium chloride of the formula:

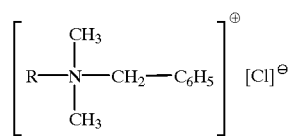

(I)

in which:

R denotes a saturated linear alkyl radical containing from 12–16 carbon atoms, or a mixture of alkyldimethylbenzylammonium chlorides of formula (I), and/or at least 0.25% by weight, relative to the total weight of the composition, of a surface-active agent, the latter being of the anionic, nonionic or amphoteric type when it is present in the aqueous phase or of the liposoluble nonionic type when it is present in the oily phase.

The dephasing agent employed in the composition of the invention is preferably a mixture of alkyldimethylbenzylammonium chloride of formula (I), consisting of approximately 65% by weight of lauryldimethylbenzylammonium chloride, approximately 23% by weight of myristyldimethylbenzylammonium chloride and approximately 8% by weight of palmityldimethylbenzylammonium chloride, the remainder consisting of at least one alkyldimethylammonium chloride in which the radical has fewer than 12 or more than 16 carbon atoms.

As a mixture of alkyldimethylbenzylammonium chlorides which can be employed in the invention there may be mentioned that marketed under the name of "benzalkonium chloride" by Fluka, the characteristics of which are the following: molecular weight=360 and melting point=35° C.

The ratio of the surface-active agent and of the dephasing agent preferably ranges from 0.1/1–200/1.

Such compositions have been described in U.S. Pat. No. 5,468,496, the content of which is incorporated hereinafter by reference.

According to an alternative form of the invention it is also possible to provide for the compositions employed in the invention to include (a) an aqueous phase including one or more surface-active agents, (b) an oily phase consisting of 50–100% of one or more dialkyl phthalate(s). Provision is preferably made for these compositions to be alcohol-free.

The aqueous phase is as described in the first alternative form of the invention.

The dialkyl phthalates employed in the compositions have the formula:

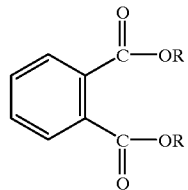

where R is $C_1$–$C_4$ alkyl, particularly methyl, ethyl or butyl.

When the dialkyl phthalate content of the oily phase is less than 100% by weight, the complement to 100% consists of one or more products which are miscible with the dialkyl phthalate.

Products miscible with the dialkyl phthalate which may be mentioned include oils, especially adipates such as dioctyl adipate, myristates such as isopropyl myristate, palmitates such as octyl palmitate, stearates such as isopropyl stearate, vitamins such as vitamin A, vitamin E and vitamin F, oils such as sunflower oil, fish oil, pentaerythritol tetra-2-ethylhexanoate and similar products.

Aesthetically attractive cosmetic compositions which are in two-phase form are obtained by employing certain surface-active agents.

When the surface-active agent dissolved in the aqueous phase is selected from anionic amphoteric and zwitterionic surface-active agents, the oily phase containing the dialkyl phthalate is to be found dispersed with stirring in the form of microbeads in the oily phase, forming a suspension which, at rest, is deposited at the bottom of the receptacle, producing a powdery effect.

When the surface-active agent in solution in the aqueous phase is selected from nonionic surface-active agents, the oily phase containing the dialkyl phthalate remains in suspension in the form of microbeads in the aqueous phase, thus giving the composition a milky appearance.

The cosmetic composition employed in this alternative form of the invention contains from 0.5–20% and preferably from 2–10% by weight of dialkyl phthalate.

The quantity of the surface-active agent is from 0.1–30% by weight and preferably from 2–6% by weight of the total weight of the composition.

Such compositions have been described in particular in U.S. Pat. No. 5,474,777.

To prepare the two-phase composition the aqueous phase may be prepared first by dissolving the water-soluble adjuvants in water. The water-insoluble solid particles may be dispersed in this aqueous phase either cold or while heating slightly and then the phase containing the dialkyl phthalate, the products which are miscible with the dialkyl phthalate and the other liposoluble adjuvants (oils, perfumes and the like) may then be poured therein. The mixture may be stirred for approximately one hour to an hour and a half and, when permitted to stand, two phases are obtained when anionic, amphoteric or zwitterionic surface-active agents are employed and a dispersion of the two phases when a nonionic surface-agent is employed.

According to another embodiment of the invention, provision may be made for the make-up removal compositions to include (a) an aqueous phase, (b) an oily phase including one or more dialkyl phthalate(s), (c) solid particles which are insoluble in the aqueous phase and in the oily phase, and (d) one or more agent(s) equilibrating the densities; the oily phase being in the form of beads which, on stirring, are dispersed homogeneously in the aqueous phase and at rest are reconstituted at the bottom of the receptacle in the form of beads. This two-phase composition, preferably alcohol-free, has an aesthetically attractive appearance. Such compositions have been described in document European Application No. 490 750.

The solid particles which are insoluble in the oily phase and in the aqueous phase are smaller than 10 $\mu$m in size. Any solid particle which is insoluble in both phases and which is maintained at the oil/water interface may be employed.

The insoluble solid particles are preferably selected from the group of inorganic and organic materials including iron oxide, titanium dioxide, antimony oxide, magnesium oxide, alumina, zinc oxide, zinc peroxide, calcium aluminate, silicic acid, magnesium silicoaluminate, talc, mica, colloidal kaolin, bentonite, zinc laurate, polyvinyl chloride, mother-of-pearl, carbon black, lanolin and mixtures thereof.

According to this embodiment of the invention the two-phase cosmetic composition also includes one or more agents equilibrating the densities, the purpose of which is to equilibrate the densities of the dialkyl phthalate phase and that of the aqueous phase. These agents which equilibrate the densities are selected from the group of products which are soluble in the aqueous phase, products which are soluble in the dialkyl phthalate and mixtures thereof. The function of the agent equilibrating the densities is to increase the density of the aqueous phase by increasing its mass without practically changing its volume or else to decrease the density of the dialkyl phthalate by increasing its volume without considerably changing its mass.

Examples of agents which equilibrate the densities, which are soluble in dialkyl phthalates, include oils, especially adipates such as dioctyl adipate, myristates such as isopropyl myristate, palmitates such as octyl palmitate, stearates such as isopropyl stearate, vitamins such as vitamin A, vitamin E and vitamin F, oils such as sunflower oil, fish oil, pentaerythritol tetra-2-ethylhexanoate and similar products.

Water-soluble agents which equilibrate the densities include water-soluble inorganic or organic salts such as trisodium phosphate, disodium phosphate, monosodium phosphate, sodium metabisulfite, magnesium sulfate, sodium sulfate, monopotassium phosphate, dipotassium phosphate, tripotassium phosphate, sodium chloride, potassium chloride, mono-, di- and trisodium citrate and, in general, water-soluble inorganic salts.

A water-soluble agent which equilibrates the densities includes a cosmetic component, for example a preserving agent, a UV screening agent, a buffer, a complexion radiance agent and in general any water-soluble compound which increases the density of water.

An agent which equilibrates the densities, which is soluble in water, and an agent which equilibrates the densities, which is soluble in the dialkyl phthalate, may be employed at the same time.

In the two-phase liquid composition the dialkyl phthalate-based phase is in the form of beads which, because of stirring, are dispersed in the form of microbeads in the aqueous phase and which are reconstituted at rest at the bottom of the aqueous phase. The insoluble solid particles place themselves at the interface of the oil beads containing the dialkyl phthalate and of the water.

The insoluble solid particles and the agents which equilibrate the densities promote the formation and the stability of the beads of oil in the water at rest.

The cosmetic composition employed in this embodiment of the invention contains from 0.5–15%, preferably from 2–10% by weight of dialkyl phthalate, from 1–10% by weight of an agent which equilibrates the densities and from 0.005–0.5%, preferably from 0.01–0.05% by weight of solid particles which are insoluble in both phases, of the total weight of the composition. The aqueous phase represents from 78–99.5%, preferably from 90–95% by weight of the total weight of the composition.

To prepare the two-phase composition, the aqueous phase may be prepared first by dissolving the agent which equilibrates the densities and the water-soluble adjuvants in water. The water-insoluble solid particles may be dispersed in this aqueous phase, either cold or with slight heating, and the phase containing the dialkyl phthalate, the agents equilibrating the density which are soluble in the dialkyl phthalate and the other liposoluble adjuvants (oils, perfumes and the like) may be poured in next. The mixture may be stirred for approximately one hour to an hour and a half and, when allowed to stand, two phases are obtained.

The compositions described above may be packaged, in a known manner, in a single-compartment bottle. The user must then shake the bottle before pouring its contents onto a swab. Provision can also be made for the two phases of the composition to be introduced into two independent compartments of a single bottle, a system being provided for mixing them at the time of the dispensing. Such devices are described, for example, in European Application No. 497256 and French Application No. 2697233.

A number of examples of use of cosmetic compositions for make-up removal according to the invention will now be given by way of illustration.

The two-phase make-up removal composition in its various embodiments described above make it possible to prepare a perfect formulation for the removal of make-up of transfer-free lip rouge and foundation compositions.

Having generally described this invention, a further understanding can be obtained by reference to certain specific examples which are provided herein for purposes of illustration only and are not intended to be limiting unless otherwise specified.

EXAMPLE 1

Two-Phase Composition

A composition is prepared including:

| | |
|---|---|
| Cyclomethicone | 28% |
| Isohexadecane | 19% |
| Poloxamer 184 (CTFA) | 0.05% |
| Phosphate buffer | 0.15% |
| Sodium chloride | 0.6% |
| Preserving agents | q.s. |
| Colorants | q.s. |
| Demineralized water | q.s. 100% |

EXAMPLE 2 (Comparative)

Single-Phase Make-Up Removal Lotion

A composition is prepared including:

| | |
|---|---|
| Disodium cocoamphodiacetate | 0.4% |
| Sodium laurate sulfate | 1% |
| Sodium laurate-8 sulfate | 1% |
| Allantoin | 0.05% |
| Hexylene glycol | 1% |
| Sodium chloride | 1% |
| Preserving agents | q.s. |
| Colorant | q.s. |
| Water | q.s. 100% |

The two compositions (Examples 1 and 2) were tested by female users (30 individuals tested) for make-up removal of two transfer-free lip rouge compositions marketed by L'Oreal under the name of Rouge Captive, one of these compositions being violet in color and the other red.

For each composition each of these users had to indicate whether it exhibited properties of coolness, of make-up removal ability and of ease of make-up removal.

The result of these tests is the following:

| | two-phase composition Example 1 | single-phase lotion Example 2 |
|---|---|---|
| Coolness | 46% | 79% |
| Ease of make-up removal | 93% | 80% |
| make-up removal ability | 93% | 80% |

These tests show that the two-phase composition contributes less coolness than the lotion. On the other hand, it is characterized by an ease of make-up removal and a make-up removal ability which are statistically significantly superior in relation to the lotion.

EXAMPLE 3 (Comparative)

Make-Up Removal Oil

A composition is prepared including:

| | |
|---|---|
| Cyclomethicone | 28% |
| Isohexadecane | 19% |
| Poloxamer 184 | 0.05% |

This make-up removal oil corresponds to the oily phase of the compositions of the invention.

This make-up removal oil was compared with the composition of Example 1 for their make-up removal ability and ease of make-up removal. The female users wore a transfer-free lip rouge marketed by L'Oreal under the name of Rouge Captive and employed the compositions of Examples 1 and 3 alternately for removing their make-up.

The make-up removal oil (Ex3) was judged to be too heavy whereas, in comparison, the two-phase composition (Ex1) provides a pleasant feeling of coolness. The make-up removal oil and the two-phase composition both have a satisfactory make-up removal ability. However, the make-up removal oil presents difficulties in use: in fact, when it is applied with the aid of a swab, the make-up removal oil "drives out" the lip rouge and makes it run beyond the lips, and this compels the user to perform a number of wipes with a swab impregnated with make-up removal oil. The users judged the ease of make-up removal with the aid of these oils as unsatisfactory, whereas the two-phase composition according to the invention was judged to be very satisfactory from this point of view. obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A method of removing a hard-to-remove make-up, comprising:
    after having applied a long-durability and/or a transfer-free lip rouge, blusher or foundation composition selected from the group consisting of:
    (i) a formulation of (a) 1–70% by wt liquid silicone resin, (b) 10–98% by weight of a volatile silicone oil and (c) pulverulent filler;
    (ii) a formulation of (a) 1–70% by wt of a volatile silicone oil, (b) 0.1–15% by wt silicone resin, (c) 10–45% by wt wax, (d) 5–50% by wt particulate filler and (e) 1–30% by wt oil;
    (iii) a formulation of a fatty phase containing phenylated silicone oil and a volatile oil; and (iv) a formulation of a volatile silicone oil and a silicone wax, to the skin, removing the applied make-up by applying a two-phase make-up remover composition, consisting essentially of:
(i) a volatile oily phase consisting of cyclic or linear silicones oils and mineral oils, and
(ii) an aqueous phase consisting of phosphate buffer, and water-soluble inorganic salt, the composition further consisting of cosmetically acceptable surface active agent, colorant and preserving agent, each of said phases existing as distinct phases, to skin covered with make-up, thereby effecting removal of said hard-to-remove make-up.

2. The method of claim 1, wherein the aqueous phase of the make-up removal composition comprises sterile demineralized water, floral water, a natural thermal or mineral water, or combinations thereof.

3. The method of claim 1, wherein the oily phase of the make-up removal composition comprises at least one silicone oil in an amount of at least 8% by weight relative to the total weight of the make-up removal composition.

* * * * *